United States Patent
Fu

[19]

[11] Patent Number: 6,090,079
[45] Date of Patent: Jul. 18, 2000

[54] SYRINGE PROTECTIVE DEVICE

[76] Inventor: Kuo Wen Fu, 6F, No. 440-2, Gin Pin Road, Chong Ho City, Taipei Hsien, Taiwan, 235

[21] Appl. No.: 09/357,109

[22] Filed: Jul. 19, 1999

[51] Int. Cl.[7] .................................................... A61M 5/00
[52] U.S. Cl. ........................... 604/198; 604/192; 604/263
[58] Field of Search ..................................... 604/198, 110, 604/263, 187, 192

[56] References Cited

U.S. PATENT DOCUMENTS

| | | | |
|---|---|---|---|
| 4,994,045 | 2/1991 | Ranford | 604/198 |
| 5,120,311 | 6/1992 | Sagstetter et al. | 604/110 |
| 5,222,945 | 6/1993 | Basnight | 604/110 |
| 5,300,038 | 4/1994 | Haber et al. | 604/198 X |
| 5,383,863 | 1/1995 | Mardones | 604/198 |

*Primary Examiner*—John D. Yasko

[57] ABSTRACT

A syringe includes a cylindrical housing slidably received in a protective cover and having a needle secured to the front end, and a plunger slidably received in the cylindrical housing. The protective cover includes a longitudinal channel and includes a groove and a depression and a cavity formed in one end. The cylindrical housing includes a latch that may be forced into the depression of the protective cover in a detachably securing position and that may be selectively forced into the cavity of the protective cover in a locking position.

6 Claims, 6 Drawing Sheets

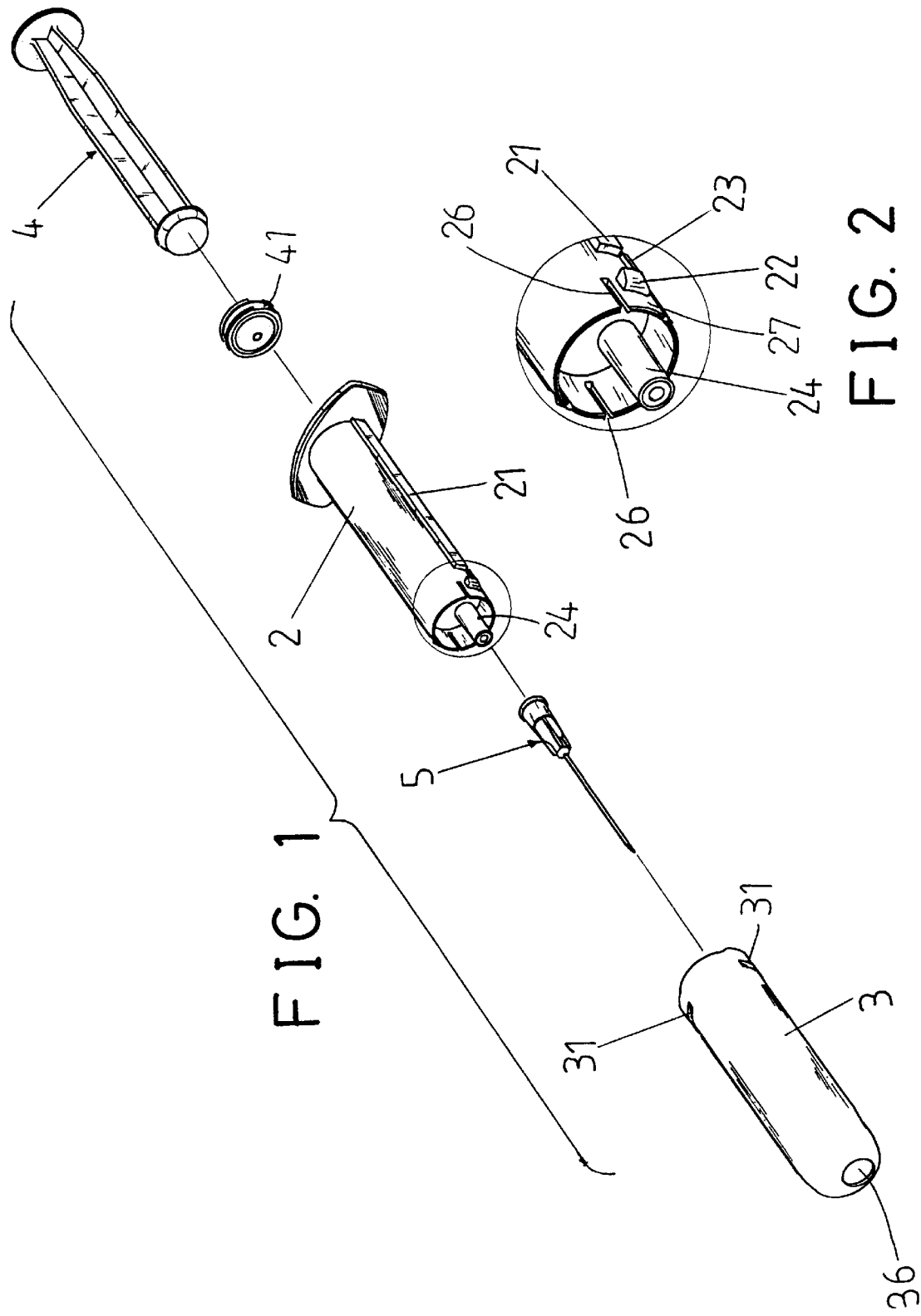

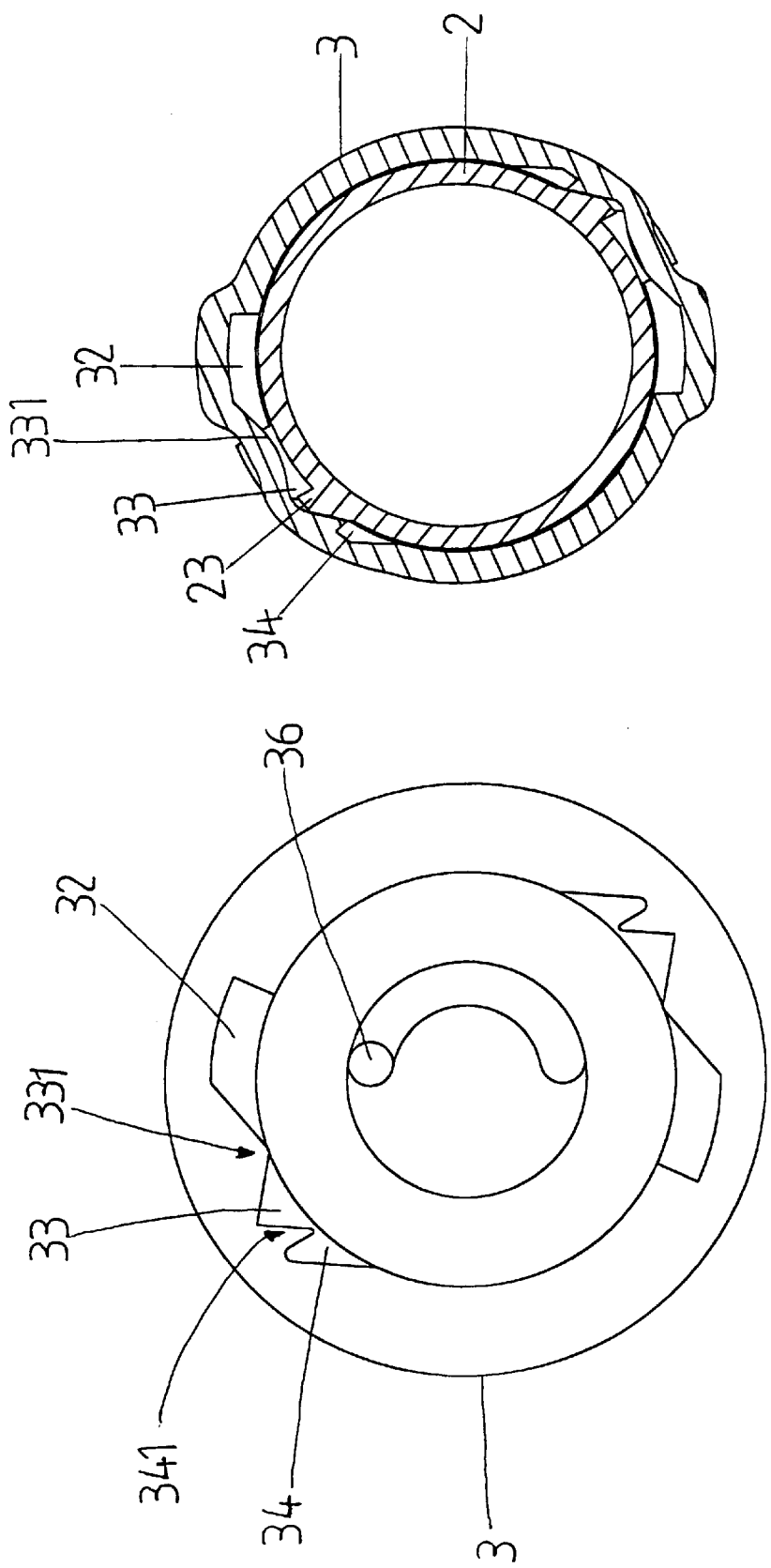

SYRINGE PROTECTIVE DEVICE

BACKGROUND OF THE INVENTION

1. Field of the Invention

The present invention relates to a syringe, and more particularly to a syringe having a protective device for protecting the syringe.

2. Description of the Prior Art

Typical syringes comprise a cylindrical body having a needle secured to one end and having a plunger slidably engaged in the other end for drawing fluid material into the cylindrical body or for injecting the fluid material outward through the needle. However, no suitable protective devices are provided for protecting or shielding the needle and for preventing the needle from hurting people inadvertently.

The present invention has arisen to mitigate and/or obviate the afore-described disadvantages of the conventional syringes.

SUMMARY OF THE INVENTION

The primary objective of the present invention is to provide a syringe including a protective device for protecting or shielding the needle and for preventing the needle from hurting people inadvertently.

In accordance with one aspect of the invention, there is provided a syringe comprising a cylindrical housing including a front portion having a cannula provided therein, a plunger slidably received in the cylindrical housing for drawing fluid material inward of the cylindrical housing and for forcing the fluid material outward of the cylindrical housing via the cannula, a protective cover including a bore formed therein for slidably receiving the cylindrical housing, and means for detachably securing the cylindrical housing to the protective cover.

The protective cover includes an inner peripheral portion having a longitudinal channel formed therein and includes a rear end having a groove formed therein and communicating with the longitudinal channel of the protective cover, the protective cover includes a depression formed in the rear end thereof, the detachably securing means includes a stop and a latch extended from the cylindrical housing and slidably engaged in the longitudinal channel of the protective cover for allowing the cylindrical housing to be engaged into the protective cover, and the latch is forced into the depression of the protective cover in a detachably securing position when the stop is slidably received in the groove of the protective cover.

The protective cover includes a cusp formed in the rear end thereof and formed between the channel and the depression for retaining the latch in the channel and the depression respectively and for allowing the latch to be moved between the channel and the depression of the protective cover.

The cylindrical housing includes a front portion having at least one slot formed therein for defining a resilient flap, the stop is extended from the resilient flap for allowing the stop to be biased to engage in the groove of the protective cover. The cylindrical housing includes a longitudinal rib formed thereon and spaced from the stop for being slidably received in the longitudinal channel of the protective cover.

The cannula is eccentric relative to the cylindrical housing, the protective cover includes a front end having an eccentric aperture formed therein, the syringe further includes a needle secured to the cannula of the cylindrical housing and aligned with the aperture of the protective cover for allowing the needle to be extended outward of the protective cover via the aperture of the protective cover when the cylindrical housing is engaged into the protective cover, and the needle is disengaged from the aperture of the protective cover when the latch is engaged into the depression of the protective cover.

A locking device is further provided for locking the cylindrical housing to the protective cover. The protective cover includes a cavity formed in the first end thereof and formed beside the depression thereof and includes a ratchet tooth formed between the depression and the cavity of the protective cover for engaging with the latch and for preventing the latch from moving backward to the depression of the protective cover when the latch is engaged into the cavity of the protective cover.

Further objectives and advantages of the present invention will become apparent from a careful reading of a detailed description provided hereinbelow, with appropriate reference to accompanying drawings.

BRIEF DESCRIPTION OF THE DRAWINGS

FIG. 1 is an exploded view of a syringe in accordance with the present invention;

FIG. 2 is a partial perspective view showing the front portion of the cylindrical body;

FIG. 5 is an end view of the protective cover;

FIGS. 9, 10, 11 are cross sectional views taken along lines 9—9, 10—10, and 11—11 of FIGS. 6, 7, 8 respectively.

DETAILED DESCRIPTION OF THE PREFERRED EMBODIMENT

Figure 7:
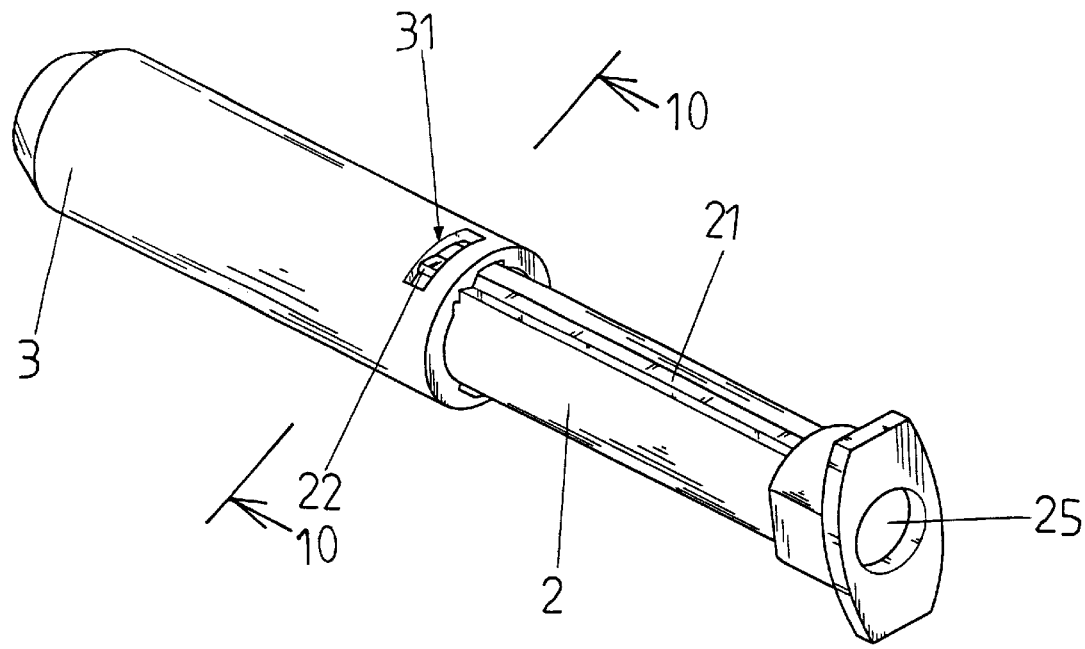
Figure 8:
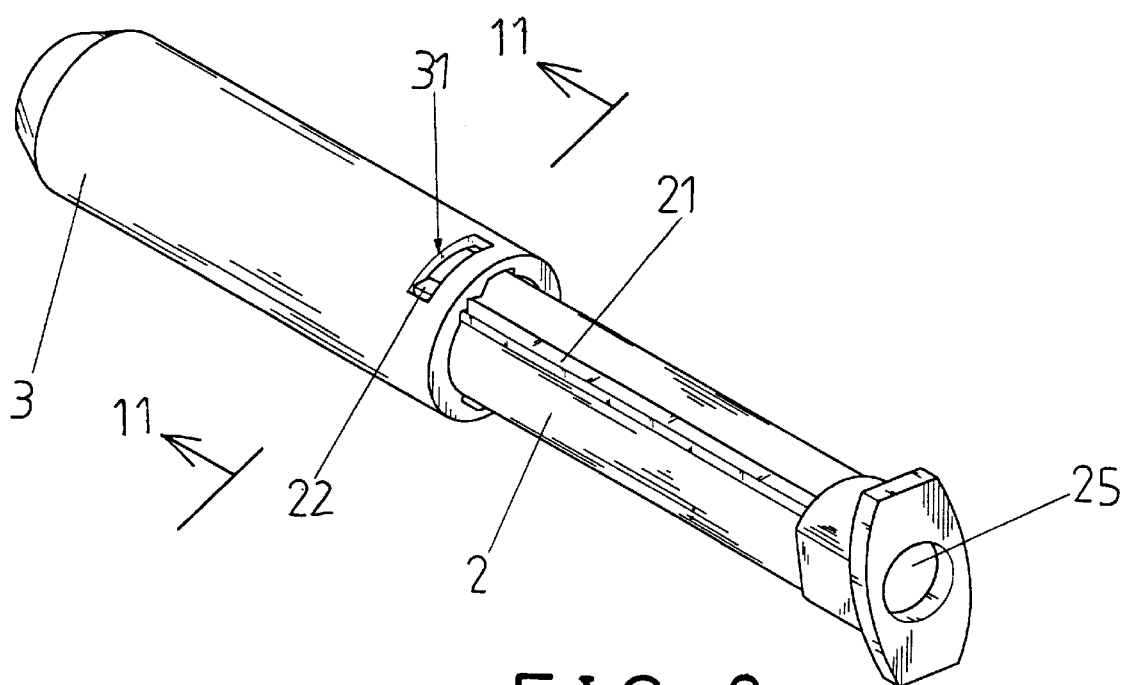

Referring to the drawings, and initially to FIGS. 1–5, a syringe in accordance with the present invention comprises a cylindrical housing or body 2 including an eccentric cannula 24 extended forward therefrom for optionally securing a needle 5 and including a bore 25 (FIGS. 6–8) formed therein for slidably receiving a plunger 4. The plunger 4 includes a piston 41 secured to the front end thereof for drawing fluid material into the cylindrical body 2 or for injecting the fluid material outward of the cylindrical body 2 through the needle 5. Without the needle 5, the fluid material may also be drawn into the cylindrical body 2 or be injected outward of the cylindrical body 2 via the cannula 24.

The protective cover 3 includes an aperture 36 formed in the front end thereof and is off-center such that the aperture 36 is eccentrically formed in the protective cover 3, best shown in FIG. 5. The protective cover 3 includes a bore 37 formed therein for slidably receiving the cylindrical body 2 and includes one or more grooves 31 laterally formed in the rear end thereof. The protective cover 3 further includes one or more longitudinal channels 32 formed in the inner peripheral portion thereof and intersecting or communicating with one end of the lateral groove 31, best shown in FIG. 4. The protective cover 3 further includes one or more depressions 33 and one or more cavities 34 formed in the rear end thereof and includes one or more cusps 331 formed between the respective channels 32 and the depressions 33 and includes one or more ratchet teeth 341 formed between the respective depressions 33 and the cavities 34. It is to be noted that the depressions 33 and the cavities 34 are formed only in the rear end portion of the protective cover 3 and do not extend across the groove 31 of the protective cover 3.

Figure 3:
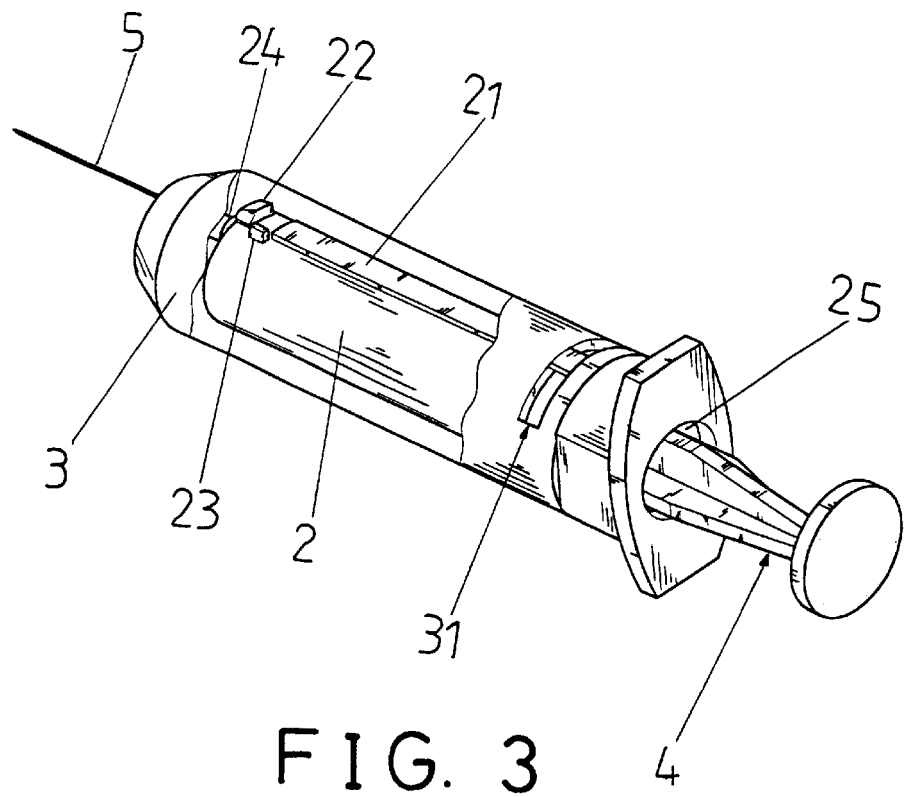
FIG. 3 is a perspective view of the syringe.

The cylindrical body 2 includes one or more pairs of parallel slots 26 formed in the front end thereof for defining one or more resilient flaps 27, and includes one or more longitudinal ribs 21 formed on the outer peripheral portion thereof and includes one or more stops 22 extended radially outward from the front end thereof and spaced from and aligned with the longitudinal ribs 21 and preferably extended from the respective resilient flaps 27 for allowing the stops 22 to be easily engaged into the channels 22 of the protective cover 3. A gap 28 (FIG. 4) is formed between the stop 22 and the rib 21. The stops 22 preferably includes a height or a thickness greater than that of the ribs 21. The resilience or the spring biasing force of the resilient flaps 27 may bias the stops 22 to slidably engage in the respective grooves 31 of the protective cover 3 (FIG. 6), and allows the stops 22 to be forced and disengaged from the respective grooves 31 and allows the stops 22 and the ribs 21 to be forced inward of the protective cover 3 through the channels 22 (FIG. 3). The cylindrical body 2 includes one or more latches 23 formed on the front end thereof and formed between the respective stops 22 and the ribs 21 and formed beside the respective gaps 28 that are formed between the stops 22 and the ribs 21. The channels 32 of the protective cover 3 have a shape corresponding to that of the stops 22 and the ribs 21 and the latches 23 for allowing the stops 22 and the ribs 21 and the latches 23 to be engaged into the channels 32 of the protective cover 3 (FIGS. 6, 9).

Figure 11:
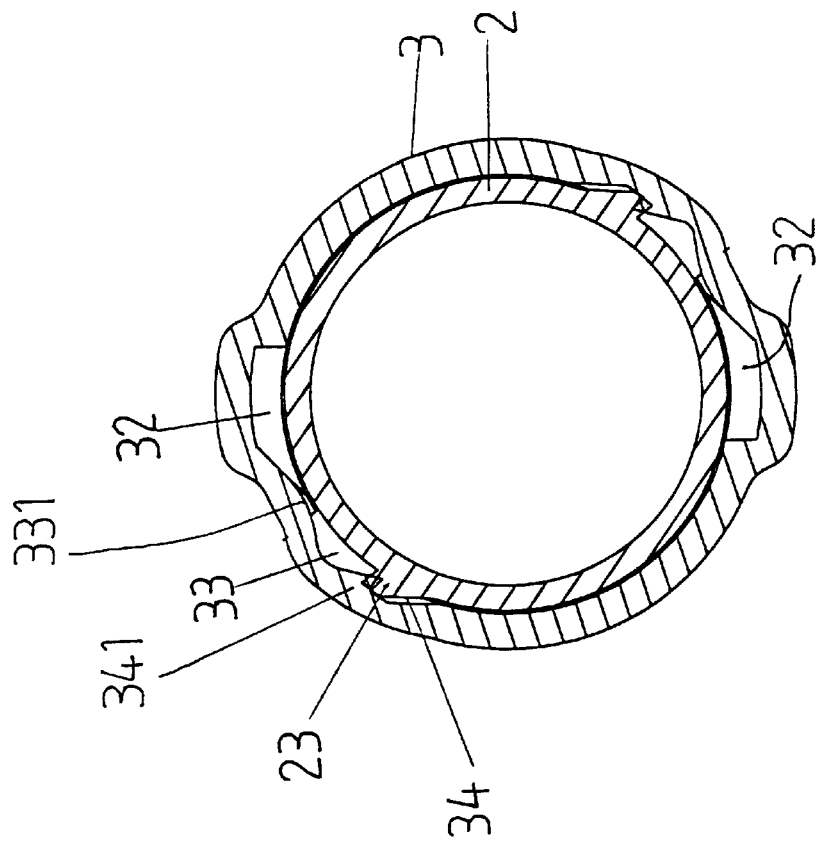

The latches 23 include a height or a thickness less than that of the stops 22 and are provided for engaging into the depressions 33 (FIGS. 7, 10) and the cavities 34 (FIGS. 8, 11) when the latches 23 are forced through the respective cusps 331 and the ratchet teeth 341 of the protective cover 3. The cusps 331 are each defined by a pair of tapered surfaces or include a curved structure for allowing the latches 23 to be moved between the channels 32 and the depressions 33 when required (FIGS. 9, 10). However, when the latches 23 are engaged into the cavities 34 of the protective cover 3, the ratchet teeth 341 may engage with and secure and lock the latches 23 in the cavities 34 and may prevent the latches 23 from being disengaged from the cavities 34 (FIG. 11).

Figure 6:
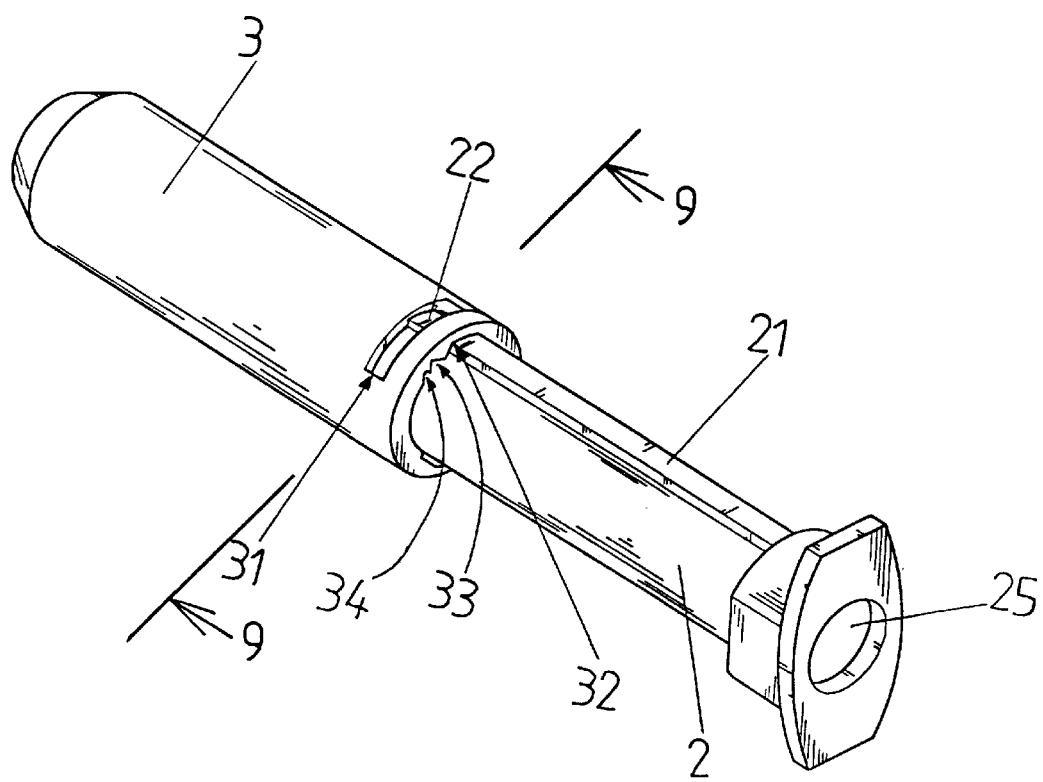
FIGS. 6, 7, 8 are perspective views illustrating the operation of the syringe.
Figure 4:
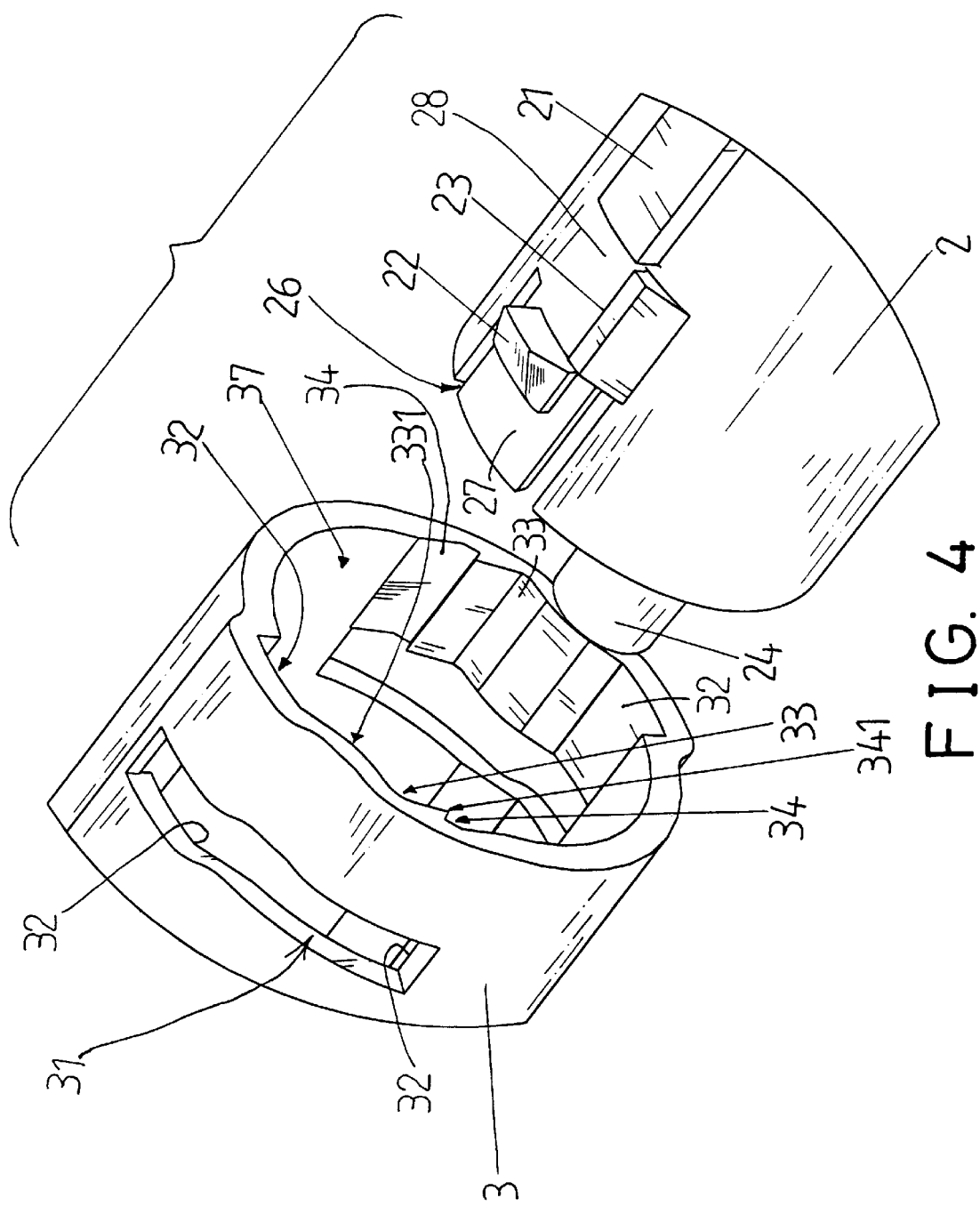
FIG. 4 is a partial exploded view illustrating the corresponding engagement structure between the protective cover and the cylindrical body.
Figure 9:
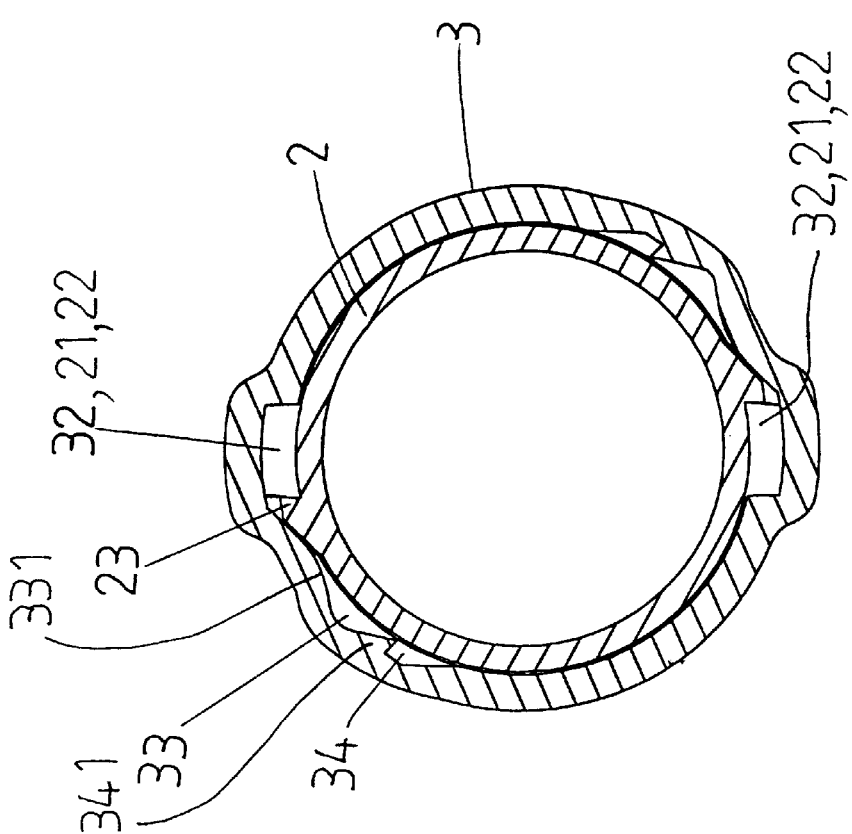

In operation, as shown in FIGS. 6 and 9, when the stops 22 and the ribs 21 and the latches 23 are aligned with the channels 32 of the protective cover 3, the cylindrical body 2 may be forced into the protective cover 3 and the needle 5 may thus be moved outward of the protective cover 3 through the eccentric aperture 36 of the protective cover 3 by forcing the ribs 21 and the stops 22 and the latches 23 into the channels 32 of the protective cover 3 (FIG. 3). The needle 5 may thus be used at this moment. When the needle 5 is not required to be used at once and may be required to be used later, the cylindrical body 2 may be moved rearward relative to the protective cover 3 until the needle 5 is received in the protective cover 3 and until the stops 22 are slidably received in the respective lateral grooves 31 of the protective cover 3. The cylindrical body 2 may further be rotated relative to the protective cover 3 for engaging the latches 23 into the respective depressions 33 of the protective cover 3 and for disengaging the needle 5 from the aperture 36 of the protective cover 3. At this moment, the latches 23 are disengaged from the respective channels 32 and the needle 5 is disengaged from the eccentric aperture 36 of the protective cover 3 such that the cylindrical body 2 may not be forced into the protective cover 3 and the needle 5 may not be moved outward of the protective cover 3 through the eccentric aperture 36 of the protective cover 3 at this moment.

When it is required to use the needle 5 again, the cylindrical body 2 may be rotated relative to the protective cover 3 for engaging the latches 23 into the respective channels 32 of the protective cover 3 again. At this moment, the cylindrical body 2 may be forced into the protective cover 3 and the needle 5 may be moved outward of the protective cover 3 through the eccentric aperture 36 of the protective cover 3 again. The engagement of the latches 23 in the respective depressions 33 of the protective cover 3 thus forms a detachably securing position. When it is no longer required to use the needle 5, the cylindrical body 2 may be rotated relative to the protective cover 3 to engage the latches 23 into the respective cavities 34 of the protective cover 3. At this moment, the latches 23 are disengaged from the respective channels 32 and the needle 5 is disengaged from the eccentric aperture 36 of the protective cover 3 such that the cylindrical body 2 may not be forced into the protective cover 3 and the needle 5 may not be moved outward of the protective cover 3. In addition, the latches 23 may not be moved inward of the depressions 33 again, such that the engagement of the latches 23 in the respective cavities 34 of the protective cover 3 forms a lock position.

Although two channels 32, two depressions 33, two cavities 34, two grooves 31, two ribs 21, two stops 22, two latches 23 and two pairs of slots 26 and two flaps 27 are shown in the drawings, for balance purposes, an engagement of a single or three or more stops and latches in the corresponding channels 32 and depressions 33 and cavities 34 and grooves 31 is good enough to conduct the above-described detachably securing operation and the locking operation.

Accordingly, the syringe in accordance with the present invention includes a protective device for protecting or shielding the needle and for preventing the needle from hurting people inadvertently.

Although this invention has been described with a certain degree of particularity, it is to be understood that the present disclosure has been made by way of example only and that numerous changes in the detailed construction and the combination and arrangement of parts may be resorted to without departing from the spirit and scope of the invention as hereinafter claimed.

I claim:

1. A syringe comprising:

a cylindrical body including a front portion having a cannula provided therein, a plunger slidably received in said cylindrical body for drawing fluid material inward of said cylindrical body and for forcing the fluid material outward of said cylindrical body via said cannula, a protective cover including a bore formed therein for slidably receiving said cylindrical body, said protective cover including an inner peripheral portion having a longitudinal channel formed therein and including a rear end having a groove formed therein and communicating with said longitudinal channel of said protective cover, said protective cover including a depression formed in said rear end thereof, means for detachably securing said cylindrical body to said protective cover, said detachably securing means including a stop and a latch extended from said cylindrical body and slidably engaged in said longitudinal channel of said protective cover for allowing said cylindrical body to be engaged into said protective cover, and said latch being forced into said depression of said protective cover in a detachably securing position when said stop is slidably received in said groove of said protective cover, and means for locking said cylindrical body to said protective cover, said locking means including a cavity formed in said first end of said protective cover and formed beside said depression and including a ratchet tooth formed between said depression and said cavity of said protective cover for engaging with said latch and for preventing said latch from moving backward to said depression of said protective cover when said latch is engaged into said cavity of said protective cover.

2. The syringe according to claim 1, wherein said protective cover includes a front end having an aperture formed therein, said syringe further includes a needle secured to said cannula of said cylindrical body and aligned with said aperture of said protective cover for allowing said needle to be extended outward of said protective cover via said aperture of said protective cover when said cylindrical body is engaged into said protective cover.

3. The syringe according to claim 1, wherein said protective cover includes a cusp formed in said rear end thereof and formed between said channel and said depression for retaining said latch in said channel and said depression respectively and for allowing said latch to be moved between said channel and said depression of said protective cover.

4. The syringe according to claim 1, wherein said cylindrical body includes a front portion having at least one slot formed therein for defining a resilient flap, said stop is extended from said resilient flap for allowing said stop to be biased to engage in said groove of said protective cover.

5. The syringe according to claim 1, wherein said cylindrical body includes a longitudinal rib formed thereon and spaced from said stop for being slidably received in said longitudinal channel of said protective cover.

6. The syringe according to claim 1, wherein said cannula is eccentric relative to said cylindrical body, said protective cover includes a front end having an eccentric aperture formed therein, said syringe further includes a needle secured to said cannula of said cylindrical body and aligned with said aperture of said protective cover for allowing said needle to be extended outward of said protective cover via said aperture of said protective cover when said cylindrical body is engaged into said protective cover, and said needle is disengaged from said aperture of said protective cover when said latch is engaged into said depression of said protective cover.

* * * * *